(12) United States Patent
Asahara et al.

(10) Patent No.: US 8,492,148 B2
(45) Date of Patent: Jul. 23, 2013

(54) METHOD FOR AMPLIFICATION OF ENDOTHELIAL PROGENITOR CELL IN VITRO

(75) Inventors: Takayuki Asahara, Kobe (JP); Haruchika Masuda, Isehara (JP)

(73) Assignees: Foundation for Biomedical Research & Innovation, Hyogo (JP); Tokai University Educational System, Tokyo (JP)

( * ) Notice: Subject to any disclaimer, the term of this patent is extended or adjusted under 35 U.S.C. 154(b) by 1212 days.

(21) Appl. No.: 11/884,949

(22) PCT Filed: Feb. 22, 2006

(86) PCT No.: PCT/JP2006/303812
§ 371 (c)(1),
(2), (4) Date: Oct. 4, 2007

(87) PCT Pub. No.: WO2006/090882
PCT Pub. Date: Aug. 31, 2006

(65) Prior Publication Data
US 2008/0166327 A1    Jul. 10, 2008

(30) Foreign Application Priority Data
Feb. 23, 2005   (JP) .................................. 2005-047816

(51) Int. Cl.
*C12N 5/00* (2006.01)
(52) U.S. Cl.
USPC ........... 435/377; 424/93.7; 435/325; 435/275
(58) Field of Classification Search
None
See application file for complete search history.

(56) References Cited

U.S. PATENT DOCUMENTS

| | | | |
|---|---|---|---|
| 5,554,512 A * | 9/1996 | Lyman et al. ................ | 435/69.5 |
| 6,306,640 B1 * | 10/2001 | Nicolette .................... | 435/252.3 |
| 7,029,666 B2 * | 4/2006 | Bruder et al. ................ | 424/93.1 |
| 2005/0084959 A1 | 4/2005 | Hamada et al. | |
| 2006/0014281 A1 * | 1/2006 | Conti et al. .................... | 435/368 |
| 2006/0030042 A1 * | 2/2006 | Brivanlou et al. ............ | 435/366 |

FOREIGN PATENT DOCUMENTS
WO    03/038076    5/2003

OTHER PUBLICATIONS

Dvorin EL et al. 2003. Quantitative evaluation of endothelial progenitors and cardiac valve endothelial cells: proliferation and differentiation on poly-glycolic acid/poly-4-hydroxybutyrate scaffold in response to vascular endothelial growth factor and transforming growth factor beta1. Tissue Eng 9: 487-493.*

Hjelmeland MD et al. 2004. SB-431542, a small molecule transforming growth factor-B-receptor antagonist, inhibits human glioma cell line proliferation and motility. Mol Cancer Ther 3: 737-745.*

R. Handgretinger et al., "Biology and Plasticity of CD133+Hematopoietic Stem Cells", Ann. N.Y. Acad. Sci., vol. 996, pp. 141-151, 2003.

B. Jazwiec et al., "Endothelial cell support of hematopoiesis is differentially altered by IL-1 and glucocorticoids", Leukemia, vol. 12, pp. 1210-1220, 1998.

M. Ishikawa et al., "Endothelial Progenitor Cell Culture for Vascular Regeneration", Stem Cells and Development, vol. 13, pp. 344-349, 2004.

J. Shin et al., "Isolation of Endothelial Progenitor Cells from Cord Blood and Induction of Differentiation by Ex Vivo Expansion", Yonsei Medical Journal, vol. 46, No. 2, pp. 260-267, 2005.

A. Treves et al., "Ex vivo Expansion of CB Derived AC 133 Progenitor Cells with a Polyamine Copper Chelator: Pre-Clinical Data", Blood, American Society of Hematology, vol. 100, No. 11, Nov. 16, 2002, Abstract #5242, p. 419B.

A. Encabo et al., "Interleukin-6 precludes the differentiation induced by interleukin-3 on expansion of CD34+cells from cord blood", Haematologica/Journal of Hematology, vol. 88, No. 4, pp. 388-395, Apr. 1, 2003.

F. Grynspan et al., "Ex-vivo Expanded Human Bone Marrow-Derived AC133⁻Cells to Treat Myocardial Infarction", Blood, American Society of Hematology, vol. 104, No. 11, pt. 1, Nov. 1, 2004, Abstract 154, p. 47A.

C. Park et al., "A hierarchical order of factors in the generation of FLK1- and SCL-expressing hematopoietic and endothelial progenitors from embryonic stem cells", Development and Disease, vol. 131, No. 11, pp. 2749-2762, Jun. 2004.

C. Urbich et al., "Endothelial Progenitor Cells: Characterization and Role in Vascular Biology", Circulation Research, vol. 95, No. 4, pp. 343-353, Aug. 20, 2004.

S. Rafii et al., "Therapeutic stem and progenitor cell transplantation for organ vascularization and regeneration", Nature Medicine, vol. 9, No. 6, pp. 702-712, Jun. 1, 2003.

T. Watabe et al., "TGF-β receptor kinase inhibitor enhances growth and integrity of embryonic stem cell-derived endothelial cells", The Journal of Cell Biology, vol. 163, No. 6, pp. 1303-1311, Dec. 22, 2003.

(Continued)

*Primary Examiner* — Lora E Barnhart Driscoll
(74) *Attorney, Agent, or Firm* — Wenderoth, Lind & Ponack, L.L.P.

(57) ABSTRACT

The present invention provides a method for expanding an endothelial progenitor cell in vitro. More particularly, the present invention provides a method for culturing a hemangioblast comprising incubating a hemangioblast in a serum-free culture medium containing one or more factors selected from the group consisting of stem cell growth factor, interleukin-6, FMS-like tyrosine kinase 3 and thrombopoietin, and a vascular endothelial cell produced by the method; and a serum-free culture medium containing one or more factors selected from the group consisting of stem cell growth factor, interleukin-6, FMS-like tyrosine kinase 3 ligand and thrombopoietin, and a kit for the preparation of the serum-free culture medium and the like.

8 Claims, 11 Drawing Sheets

OTHER PUBLICATIONS

K. Ducos et al., "p21$^{cip1}$ mRNA is Controlled by Endogenous Transforming Growth Factor-β1 in Quiescent Human Hematopoietic Stem/Progenitor Cells", Journal of Cellular Physiology, vol. 184, No. 1, pp. 80-85, Jul. 1, 2000.

T. Asahara et al., "Isolation of Putative Progenitor Endothelial Cells for Angiogenesis", Science, vol. 275, pp. 964-967, Feb. 14, 1997.

C. Kalka et al., "Transplantation of Ex Vivo Expanded Endothelial Progenitor Cells for Therapeutic Neovascularization", PNAS, vol. 97, No. 7, pp. 3422-3427, Mar. 28, 2000.

A. Kawamoto et al., "Therapeutic Potential of Ex Vivo Expanded Endothelial Progenitor Cells for Myocardial Ischemia", Circulation, vol. 103, pp. 634-637, 2001.

Japanese Office Action issued Nov. 8, 2011, in corresponding Japanese Patent Application No. 2007-504837.

Wu X et al. Tissue-engineered microvessels on three-dimensional biodegradable scaffolds using human endothelial progenitor cells. Am J Physiol Heart Circ Physiol. Aug. 2004;287(2):H480-7.

Shin J et al. Isolation of Endotheliel Progenitor Cells From Human Cord Blood and Differentiation In Vitro to Endothelial Cells. Transfusion 41, suppl., p. 2S (Abstract P6-020B) 2001.

Loges S et al. Identification of the adult human hemangioblast. Stem Cells Dev. Jun. 2004;13(3):229-42.

Masuda H et al. Post-natal endothelial progenitor cells for neovascularization in tissue regeneration. Cardiovasc Res. May 1, 2003;58(2):390-8.

Peichev M et al. Expression of VEGFR-2 and AC133 by circulating human CD34(+) cells identifies a population of functional endothelial precursors. Blood. Feb. 1, 2000;95(3):952 8.

* cited by examiner

METHOD FOR AMPLIFICATION OF ENDOTHELIAL PROGENITOR CELL IN VITRO

TECHNICAL FIELD

This application is a U.S. national stage of International Application No. PCT/JP2006/303812 filed Feb. 22, 2006.

The present invention relates to a method for culturing hemangioblasts, and an endothelial progenitor cell obtainable by the method and the like.

BACKGROUND ART

Targeting ischemic cardiac diseases, a bone marrow mononuclear cell transplantation therapy and a cell transplantation therapy using endothelial progenitor cells (hereinafter to be also abbreviated as EPC) by collecting peripheral-blood stem cells have been applied in recent years. However, some problems such as those mentioned below have been clarified.
1) Any existing therapy causes physical burden on patients, such as systemic anesthesia, administration of granulocyte colony stimulating factor (G-CSF), apheresis and the like.
2) Repetitive transplantation therapy is difficult.
3) Since supply of qualitatively and quantitatively sufficient cells necessary for transplantation is sometimes difficult to secure, a sufficient therapeutic effect is difficult to obtain.

DISCLOSURE OF THE INVENTION

An object of the present invention is to provide a method for expanding functional undifferentiated endothelial progenitor cells in vitro, and an endothelial progenitor cell for cell transplantation obtainable by the method.

In view of the above-mentioned problems, the present inventors have studied cultivation conditions permitting undifferentiated endothelial progenitor cells to differentiate and expand in vitro. As a result, the present inventors have succeeded in efficient expansion of EPC in vitro by culturing a hemangioblast in a serum-free culture medium containing a factor selected from the group consisting of (1) a stem cell factor (SCF), (2) interleukin-6 (IL-6), (3) FMS-like tyrosine kinase 3 (Flt-3 ligand) and (4) thrombopoietin (TPO), and more efficient expansion of EPC by further adding (5) a vascular endothelial growth factor (VEGF), and/or (6) a transforming growth factor β (TGF-β) inhibitor to the medium and the like, which resulted in the completion of the present invention.

Accordingly, the present invention provides the following:
[1] a method for culturing a hemangioblast, which comprises incubating the hemangioblast in a serum-free culture medium containing a stem cell factor, interleukin-6, FMS-like tyrosine kinase 3 and thrombopoietin;
[2] the method of the above-mentioned [1], which is a method for expanding an endothelial progenitor cell, wherein the endothelial progenitor cell is expanded by incubation of the hemangioblast;
[3] the method of the above-mentioned [1], wherein the hemangioblast is derived from bone marrow, cord blood or peripheral blood;
[4] the method of the above-mentioned [1], wherein the hemangioblast is a mononuclear cell;
[5] the method of the above-mentioned [1], wherein the hemangioblast is CD34 positive and/or CD133 positive;
[6] the method of the above-mentioned [1], wherein the hemangioblast and various factors to be added to the serum-free culture medium are derived from animals of the same species;
[7] the method of the above-mentioned [1], wherein the hemangioblast is derived from human;
[8] the method of the above-mentioned [1], wherein the serum-free culture medium further comprises a vascular endothelial growth factor and/or a transforming growth factor β inhibitor;
[9] an endothelial progenitor cell obtainable by the method of the above-mentioned [2];
[10] a composition comprising an endothelial progenitor cell obtainable by the method of the above-mentioned [2], and substantially free of a biological component derived from an animal of a different species from the animal, from which the endothelial progenitor cell is derived;
[11] the composition of the above-mentioned [10], which is used for allogeneic transplantation;
[12] the composition of the above-mentioned [11], wherein the endothelial progenitor cell is derived from human;
[13] the composition of the above-mentioned [12], which is an agent for the prophylaxis or treatment of an ischemic disease;
[14] a serum-free culture medium containing a stem cell factor, interleukin-6, FMS-like tyrosine kinase 3 ligand and thrombopoietin;
[15] a kit for preparing a serum-free culture medium containing a stem cell factor, interleukin-6, FMS-like tyrosine kinase 3 ligand and thrombopoietin, which comprises a stem cell factor, interleukin-6, FMS-like tyrosine kinase 3 ligand, thrombopoietin and a serum-free culture medium (at least one factor from a stem cell factor, interleukin-6, FMS-like tyrosine kinase 3 ligand and thrombopoietin is not contained in the serum-free culture medium).

By transplanting a cell expanded by the method of the present invention, the cardiac function (contractile function and diastolic function) in ischemic cardiac disease was improved. That is, the method of the present invention is considered to be useful for both qualitatively and quantitatively producing an endothelial lineage cell, and can be a useful method for cell transplantation therapy targeting vascular disorders such as ischemic cardiac diseases and the like.

BEST MODE FOR EMBODYING THE INVENTION

Figure 1:
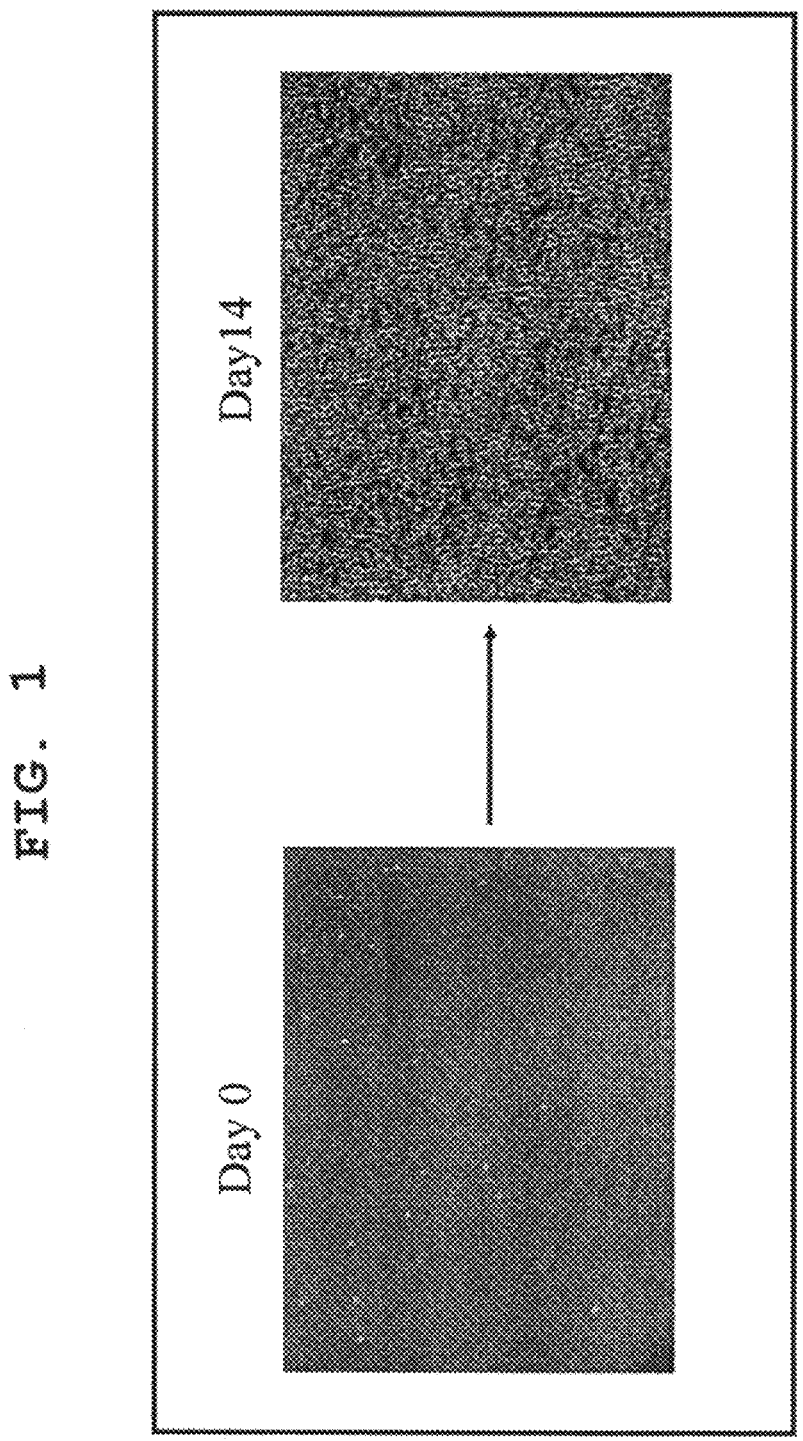
FIG. 1 shows the state of cord blood-derived CD133 positive cells after culture in the serum-free culture medium of the present invention (1 μM of TGF-β inhibitor) for 14 days.

The present invention provides a novel method for culturing a hemangioblast. The cultivation method of the present invention comprises incubating a hemangioblast in a serum-free culture medium containing one or more, preferably not less than 3, more preferably all, factors selected from the group consisting of SCF, IL-6, Flt-3 ligand and TPO. Accordingly, the serum-free culture medium used in the cultivation method of the present invention may contain, for example, a) SCF, b) IL-6, c) Flt-3 ligand, d) TPO, e) a combination of SCF and IL-6, f) a combination of SCF and Flt-3 ligand, g) a combination of SCF and TPO, h) a combination of IL-6 and Flt-3 ligand, i) a combination of IL-6 and TPO, j) a combination of Flt-3 ligand and TPO, k) a combination of SCF, IL-6 and Flt-3 ligand, l) a combination of SCF, IL-6 and TPO, m) a combination of SCF, Flt-3 ligand and TPO, n) a combination of IL-6, Flt-3 ligand and TPO, or o) a combination of SCF, IL-6, Flt-3 ligand and TPO.

The "hemangioblast" used in the present invention refers to a progenitor cell of both blood lineage cell and vascular endothelial cell, and is not particularly limited as long as it is an undifferentiated cell, which can be a blood lineage cell (e.g., red blood cell, T-lymphocyte, B-lymphocyte, monocyte/macrophage, granulocyte, megakaryocyte) via a blood stem cell or blood progenitor cell, or can be a vascular endothelial cell via EPC. As the hemangioblast, a cell derived from bone marrow, cord blood or peripheral blood of a test subject can be used. The hemangioblast may also be a mononuclear cell.

Moreover, the hemangioblast may be CD34 and/or CD133 positive. Accordingly, as the hemangioblast, use of only preliminarily selected CD34 positive and/or CD133 positive cells is also preferable. For selection of CD34 positive and/or CD133 positive cells, cell sorting methods generally used in the art are used. Specifically, magnetic cell sorting method (MACS), fluorescent cell sorting method (FACS) and the like, which use a substance having specific affinity to CD34 antigen and/or CD133 antigen, can be mentioned.

As the substance having specific affinity to CD34 antigen or CD133 antigen, for example, an antibody having specific affinity to these proteins or a fragment thereof can be mentioned. The specific affinity means the ability to specifically recognize and bind to the protein by antigen-antibody reaction. The antibody or fragment thereof is not particularly limited as long as it can specifically bind to the protein. It may be a polyclonal antibody, monoclonal antibody or functional fragment thereof. These antibody or functional fragment thereof can be produced by methods generally used in the art. For example, when a polyclonal antibody is used, a method comprising injecting the protein subcutaneously on the back, intraperitoneally, intravenously or the like to an animal such as mouse and rabbit to immunize the animal and, after increase of the antibody titer, collecting the antiserum can be mentioned. When a monoclonal antibody is used, a method comprising producing hybridoma according to a conventional method and collecting a secretory fluid thereof can be mentioned. As a method of producing an antibody fragment, a method comprising expression of a cloned antibody gene fragment in a microorganism and the like is frequently used. The purity of the antibody, antibody fragment and the like is not particularly limited as long as it maintains specific affinity to the protein. The antibody and fragment thereof may be labeled with a fluorescent substance, enzyme, radioisotope or the like.

The animal species from which the cell used in the present invention is derived means a mammal in general including human, to whom the cell transplantation therapy for a disease such as ischemic cardiac diseases and the like is applied. However, in view of the object of the present invention, i.e., clinical application, it is preferably human.

As the "serum-free culture medium" to be used in the present invention, any medium generally used in the art can be utilized. For example, a serum-free culture medium known as a medium for growth of hematopoietic stem cells can be used. As the basal medium used as the serum-free culture medium, for example, DMEM, MEM, IMDM and the like can be mentioned.

The stem cell factor (SCF) to be used in the present invention is a glycoprotein with about 30,000 of molecular weight, consisting of 248 amino acids. While there exist a soluble form and a membrane-bound form due to alternative splicing, SCF used in the present invention may be of any form, as long as it is useful for cultivation of a hemangioblast. It is preferably of a soluble form. While the derivation and the like of SCF are not particularly limited, a recombinant expected to ensure a stable supply is preferable, and a human recombinant is particularly preferable. Commercially available ones are known. The concentration of SCF in the serum-free culture medium varies depending on the kind of SCF to be used, and is not particularly limited as long as it is useful for cultivation of a hemangioblast. When human recombinant SCF is used, the concentration is, for example, 10-1000 ng/mL, preferably 50-500 ng/mL, more preferably about 100 ng/mL.

Interleukin-6 (IL-6) to be used in the present invention is a glycoprotein with 210,000 of molecular weight, isolated as a factor introducing terminal differentiation of a B cell into an antibody-producing cell, and known to be involved in immune response, proliferation and differentiation of a hematopoietic lineage or neural lineage cell, acute-phase reaction and the like. While IL-6 to be used in the present invention can be appropriately selected, when it is used for culturing human hemangioblast, human IL-6 is preferable, and a recombinant expected to ensure a stable supply is particularly preferable. Commercially available ones are known. The concentration of IL-6 in the serum-free culture medium varies depending on the kind of IL-6 to be used, and is not particularly limited as long as it is useful for cultivation of a hemangioblast. When human recombinant IL-6 is used, the concentration is, for example, 1-500 ng/mL, preferably 5-100 ng/mL, more preferably about 20 ng/mL.

FMS-like tyrosine kinase 3 ligand (Flt-3 ligand) to be used in the present invention is known as a receptor tyrosine kinase that plays an important role in the initial hemopoietic regulation. While some products resulting from alternative splicing are known, they are reported to stimulate the growth of a hematopoietic lineage stem cell. Flt-3 ligand to be used in the present invention may be any type of Flt-3 ligand as long as it is useful for cultivation of a hemangioblast. Commercially available ones are known. The concentration of Flt-3 ligand in the serum-free culture medium varies depending on the kind of Flt-3 ligand to be used, and is not particularly limited as long as it is useful for cultivation of a hemangioblast. When human recombinant Flt-3 ligand is used, the concentration is, for example, 10-1000 ng/mL, preferably 50-500 ng/mL, more preferably about 100 ng/mL.

Thrombopoietin (TPO) to be used in the present invention is a kind of hematopoietic cytokine, and known to specifically act on the process of producing megakaryocyte from hematopoietic stem cell to promote production of megakaryocyte. While the derivation and the like of TPO to be used in the present invention are not particularly limited, a recombinant expected to ensure a stable supply is preferable, and a human recombinant is particularly preferable. Commercially available ones are known. The concentration of TPO in the serum-free culture medium varies depending on the kind of TPO to be used, and is not particularly limited as long as it is useful for cultivation of a hemangioblast. When human recombinant TPO is used, the concentration is, for example, 1-500 ng/mL, preferably 5-100 ng/mL, more preferably about 20 ng/mL.

The serum-free culture medium to be used in the present invention may further contain a VEGF and/or TGFβ inhibitor in addition to one or more factors selected from the group consisting of the above-mentioned SCF, IL-6, Flt-3 ligand and TPO, since it is more beneficial for cultivation of a hemangioblast (e.g., more efficient expansion of EPC or increased total number of expanded cells).

The vascular endothelial growth factor (VEGF) which can be used in the present invention is a growth factor specifically acting on EPC, and known to be mainly produced in a perivascular cell. Several kinds of VEGF proteins having different sizes are produced by alternative splicing. The VEGF to be used in the present invention may be any type of VEGF as long as it enables colony formation of EPC. It is preferably $VEGF_{165}$. While the derivation and the like of VEGF are not particularly limited, a recombinant expected to ensure a stable supply is preferable, and a human recombinant is particularly preferable. Commercially available ones are known. The concentration of VEGF in the serum-free culture medium varies depending on the kind of VEGF to be used, and is not particularly limited as long as it is useful for cultivation of a hemangioblast. When human recombinant $VEGF_{165}$ is used, the concentration is, for example, about 5-500 ng/mL, preferably about 20-100 ng/mL, more preferably about 50 ng/mL.

A TGF-β inhibitor may also be used in the present invention. TGF-β is a protein having a 25 kDa dimer structure. In mammal, three kinds of isoforms (TGF-β1, β2 and β3) having similar structures are known to be present. It is known as a growth inhibitory factor for many cells. TGF-β inhibitor to be used in the present invention may inhibit any isoform as long as it enables expansion of EPC in vitro. Preferably, SB-431542 can be used. SB-431542 is also known as 4-(5-benzo[1.3]dioxol-5-yl-4-pyridin-2-yl-1H-imidazol-2-yl)-benzamide (see, Molecular Pharmacology 62 (1):65-74 (2002)). Commercially available ones are known. The concentration of TGF-β inhibitor in the serum-free culture medium varies depending on the kind of TGF-β inhibitor to be used, and is not particularly limited as long as it is useful for cultivation of a hemangioblast. When SB-431542 is used, it is, for example, about 0.1-10 μM, preferably about 0.5-5 μM, more preferably about 1 μM.

It is preferable to use various factors to be added to the serum-free culture medium of the present invention, which have been derived from the same species of animal as the animal from which the hemangioblast is derived. By unifying the derivation of the hemangioblast and various factors, a cell culture suitable for allogeneic transplantation such as allograft and the like can be obtained. In addition, using a hemangioblast derived from an individual who intends to undergo a cell transplantation, a cell culture suitable for syngeneic transplantation can also be obtained. In this way, since a hemangioblast can be cultured in an environment completely free of a component derived from an animal of a different species, the obtained cell culture is advantageous in that a risk of infection and rejection on transplantation and the like can be avoided.

In the present invention, a particularly preferable serum-free culture medium is one containing about 50 ng/ml VEGF, about 100 ng/mL SCF, about 20 ng/mL IL-6, 100 ng/mL Flt-3 ligand, about 20 ng/mL TPO and about 10 μM TGF-β inhibitor.

Each of the above-mentioned components is dissolved in a serum-free culture medium to a given concentration, or a concentrated solution of each component (stock solution) is prepared in advance and diluted with a serum-free culture medium to a given concentration, whereby the serum-free culture medium of the present invention to be used for the expansion of EPC in vitro can be prepared. For example, the serum-free culture medium of the present invention can be prepared by dissolving the necessary components in a commercially available serum-free culture medium to given concentrations and sterilizing the medium by filtration and the like, or aseptically adding the stock solutions sterilized by filtration and the like to a commercially available serum-free culture medium to dilute them. Sterilization by filtration can be performed according to a method generally employed in the art. For example, it is performed using 0.22 μm or 0.45 μm of Millipore filter and the like.

A hemangioblast can be cultured in a serum-free culture medium containing the aforementioned factors by adding a cell suspension containing the hemangioblast to the serum-free culture medium containing the aforementioned factors. As the cell suspension, a body fluid itself containing a hemangioblast (e.g., bone marrow fluid, cord blood, peripheral blood) can also be used. The cultivation conditions for a hemangioblast are not particularly limited, and those generally employed in the art can be utilized. For example, cultivation is performed under a 5% $CO_2$ atmosphere at 37° C. for not less than 7 days (e.g., not less than 10 days). The concentration of a hemangioblast in a serum-free culture medium is not particularly limited as long as it allows cultivation of the hemangioblast. For example, it is $0.5$-$10 \times 10^5$ cells/ml, more preferably about $1$-$5 \times 10^5$ cells/ml, most preferably about $3$-$4 \times 10^5$ cells/ml.

In one embodiment, the cultivation method of the present invention may be a method for the expansion of hemangioblast or EPC. The "expansion" of a cell means increasing the number of cells while maintaining the undifferentiated state of the cell as long as possible. A hemangioblast or EPC can be expanded by culturing the hemangioblast using the aforementioned factors at, for example, the aforementioned concentrations. According to the expansion method of the present invention, the number of hemangioblasts can be increased, and the number of EPC derived from the hemangioblast can be increased.

In another embodiment, the cultivation method of the present invention enables promotion of differentiation of hemangioblast into vascular lineage cell (e.g., EPC), or suppression of differentiation of hemangioblast into blood lineage cell. According to the cultivation method of the present invention, a hemangioblast can be more certainly destined to be a vascular lineage cell. Promotion of differentiation of hemangioblast into vascular lineage cell, and suppression of differentiation of hemangioblast into blood lineage cell can be accomplished by culturing a hemangioblast using the aforementioned factors at, for example, the aforementioned concentrations.

A decrease of blood lineage cells and increase of EPC by the method of the present invention can be confirmed, for example, by determining the blood lineage cell colony-forming ability and EPC colony-forming ability of the obtained cell suspension.

The blood lineage cell colony-forming ability can be determined by a method generally used in the art. Specifically, it can be determined by a colony assay of hematopoietic stem cell using a methylcellulose-based medium for measurement of hematopoietic progenitor cell colony (e.g., MethoCult) available from Stem Cell. Technology, Inc. etc. As the kit for determining blood lineage cell colony-forming ability, for example, a kit manufactured by Stem Cell. Technology, Inc. (catalog No. H4335) is commercially available.

The EPC colony-forming ability can be determined using a methylcellulose medium containing a physiologically active substance, specifically vascular endothelial growth factor (VEGF) and basic fibroblast growth factor (bFGF), preferably further containing 1 or not less than 2, preferably not less than 3, more preferably all, factors selected from the group consisting of stem cell factor (SCF), interleukin 3 (IL-3), insulin growth factor (IGF) and epithelial growth factor (EGF) in addition to the above-mentioned factors, and further containing a serum and/or heparin as necessary. Particularly preferably, EPC colony is formed by cultivation in a methylcellulose medium containing about 30% serum, about 50 ng/mL VEGF, about 100 ng/mL SCF, about 20 ng/mL IL-3, about 2 U/mL heparin, about 50 ng/mL b-FGF, about 50 ng/mL EGF and about 50 ng/mL IGF, under a 5% $CO_2$ atmosphere at 37° C. generally for not less than 10 days, for example, for 14-18 days or longer. While formation of colony can be visually confirmed, whether or not the obtained colony indeed consists of EPC is determined by confirming the ability of acetylated LDL (acLDL) uptake, bindability with UEA-1 lectin, expression of VE-cadherin, KDR, vWF (e.g., by RT-PCR or fluorescence immunohistochemical analysis) and the like. For example, when a colony is double-stained with DiI-labeled acetylated LDL (acLDL-DiI) and FITC-labeled UEA-1 lectin (UEA-1 lectin-FITC), the colony is double-stained in the case of EPC.

To determine the degree of differentiation of EPC, two kinds of colonies having different sizes, namely, an endothelial cell-like large cell colony (CFU-Large cell like EC, also referred to as large cell colony) mainly including cells with 20-50 μm of diameter and an endothelial cell like small cell colony (CFU-small cell like EC, also referred to as small cell colony) mainly including cells with 20 μm or below of diameter are measured separately. An endothelial cell-like small cell colony that appears in an early stage is an EPC colony in an early differentiation stage, and an endothelial cell-like large cell colony that appears in a later stage is an EPC colony in a late differentiation stage. The "mainly" used herein means that about 30%, preferably about 50%, particularly preferably about 70%, of the cell population constituting the colony are cells with 20-50 μm of diameter (for large cell colony) or cells with 20 μm or below of diameter (for small cell colony).

The EPC colony-forming ability can also be determined using a commercially available kit. As such kit, for example, a kit manufactured by Stem Cell. Technology, Inc. (catalog No. H4236) is commercially available. Using the medium of the kit supplemented with each of the aforementioned factors, the EPC colony-forming ability can be conveniently determined.

The present invention further provides a method for preparing a vascular endothelial cell, which comprises differentiating EPC obtained by the cultivation method of the present invention into vascular endothelial cell. EPC can be differentiated into vascular endothelial cell by a method known per se. For example, a method using EBM-2, EGM2V Single Quots (Clonetics Inc.), autologous serum and the like can be mentioned.

The cells such as hemangioblast, EPC, vascular endothelial cell and the like, which are obtainable by the method of the present invention, can be appropriately isolated and/or purified. For example, CD34 and CD133 as a cell surface marker of hemangioblast, KDR as a cell surface marker of EPC, and KDR and vascular endothelial cadherin as a surface marker of vascular endothelial cell are known. Therefore, desired cells can be separated by applying cells to a cell separation method using a substance (e.g., antibody) having affinity to these cell surface markers. As such cell separation method, for example, magnetic cell sorting method (MACS) and fluorescent cell sorting method (FACS) can be mentioned.

The present invention also provides a cell obtainable by the method of the present invention. As the cell obtainable by the method of the present invention, for example, hemangioblast, EPC and vascular endothelial cell can be mentioned. By unifying the derivation of hemangioblast and various factors to be used in the method of the present invention, a composition (cell culture) substantially free of a biological component derived from a different animal species can be obtained. As used herein, the composition "substantially" free of a biological component derived from a different animal species means the quality affordable by culturing cells without using a biological component from a different animal species. In addition, using a hemangioblast derived from an individual who intends to undergo a cell transplantation, a composition suitable for syngeneic transplantation can also be obtained. Accordingly, the cell of the present invention is advantageous in that a risk of infection and rejection on transplantation and the like can be avoided.

The EPC and vascular endothelial cell obtainable by the method of the present invention can be used for the treatment of vascular disorders by way of cell transplantation. As such vascular disorder, for example, ischemic diseases (e.g., ischemic cardiac diseases such as myocardial infarction, angina pectoris and the like, limb ischemia such as limb ischemic arteriosclerosis and the like, Burger disease), and vascular injury can be mentioned. It can also be used for curing a wound such as skin ulcer and the like or producing an artificial blood vessel. The effect after cell transplantation can be confirmed by a method known per se. For example, when the vascular disorder is an ischemic cardiac disease, the post-transplant cardiac function can be evaluated, for example, by determining the contractile function and diastolic function. The contractile function or diastolic function of the heart can be determined by various methods used in the art. For example, the contractile function can be determined by measuring +dp/dt value (which decreases as the contractile function decreases) calculated from the mitral regurgitation waveform or left ventricular ejection fraction (% EF, which decreases as the contractile function decreases) and the like. The diastolic function can be similarly determined by measuring –dp/dt value (which increases as the diastolic function decreases) calculated from mitral regurgitation waveform or end-diastolic inner diameter (EDd) and the like (e.g., see FASEB Journal, 18:1392-1394 (2004)).

The present invention further provides a serum-free culture medium containing the aforementioned factors, and a reagent for cultivation of hemangioblast, comprising the serum-free culture medium.

The present invention also provides a kit comprising SCF, IL-6, Flt-3 ligand, TPO and a serum-free culture medium. The kit of the present invention contains at least one factor from SCF, IL-6, Flt-3 ligand and TPO in a form isolated from the serum-free culture medium, for example, stored in a different container. In addition to SCF, IL-6, Flt-3 ligand and TPO, VEGF and/or TGFβ inhibitor may also be provided in a form isolated from the serum-free culture medium, or added to the serum-free culture medium. The kit of the present invention can be useful, for example, for producing the serum-free culture medium of the present invention.

The kit of the present invention may further contain a substance (e.g., antibody) having specific affinity to the cell surface marker of a hemangioblast or differentiated cell thereof (e.g., EPC, vascular endothelial cell), and/or a differentiation-inducing factor of a hemangioblast or differentiated cell thereof (e.g., factor inducing the differentiation from EPC into vascular endothelial cell). Such kit is preferably used in the cultivation method of the present invention.

The present invention is explained in more detail in the following by referring to the Examples, which are described for explanation of the present invention and do not limit the present invention in any way.

EXAMPLES

Example 1

Expansion from Cord Blood CD133 Positive Cell (1) Preparation of Serum-Free Culture Medium of the Present Invention The serum-free culture medium of the present invention was produced according to the composition shown in Table 1 and using a serum-free culture medium (STEMSPAN, Stem Cell Tec.). To be specific, each of the ingredients shown in Table 1 was aseptically added to a serum-free culture medium to a given concentration.

TABLE 1

| component | provided by | concentration |
| --- | --- | --- |
| hrVEGF | Peprotec | 50 ng/mL |
| hrSCF | Kirin Brewery | 100 ng/mL |
| hrIL-6 | Kirin Brewery | 20 ng/mL |
| hrFlt-3 | Peprotec | 100 ng/mL |
| hrTPO | Kirin Brewery | 20 ng/mL |

In Table 1, "h" shows human derivation. "r" shows a recombinant. Other abbreviations are as mentioned above.

Serum-free culture media were produced by further adding a TGF-β inhibitor to the above-mentioned serum-free culture medium to a concentration of 0 μM, 0.1 μM, 1 μM and 10 μM, respectively. SB-431542 (TGFβ1-type receptor kinase activity inhibitor) provided by Kirin Brewery Company was used as TGF-β.

(2) In Vitro Expansion of EPC

As the cell suspension containing hemangioblastm, a cell suspension containing cord blood-derived mononuclear cells was used. First, the collected blood was overlaid on Histopaque-1077, and mononuclear cells were separated by density-gradient centrifugation. The separated mononuclear cells were washed with PBS-EDTA. The platelet was removed, and the mononuclear cells were collected and suspended in buffer to give a cell suspension.

Then, the cell suspension was subjected to MACS using anti-CD133 antibody and CD133 positive cells were recovered. For detail, a CD133 positive cell isolation kit (manufactured by Militenyi Biotec, catalog No.130-050-801) was used, and the protocol of the package insert was followed.

Figure 2:
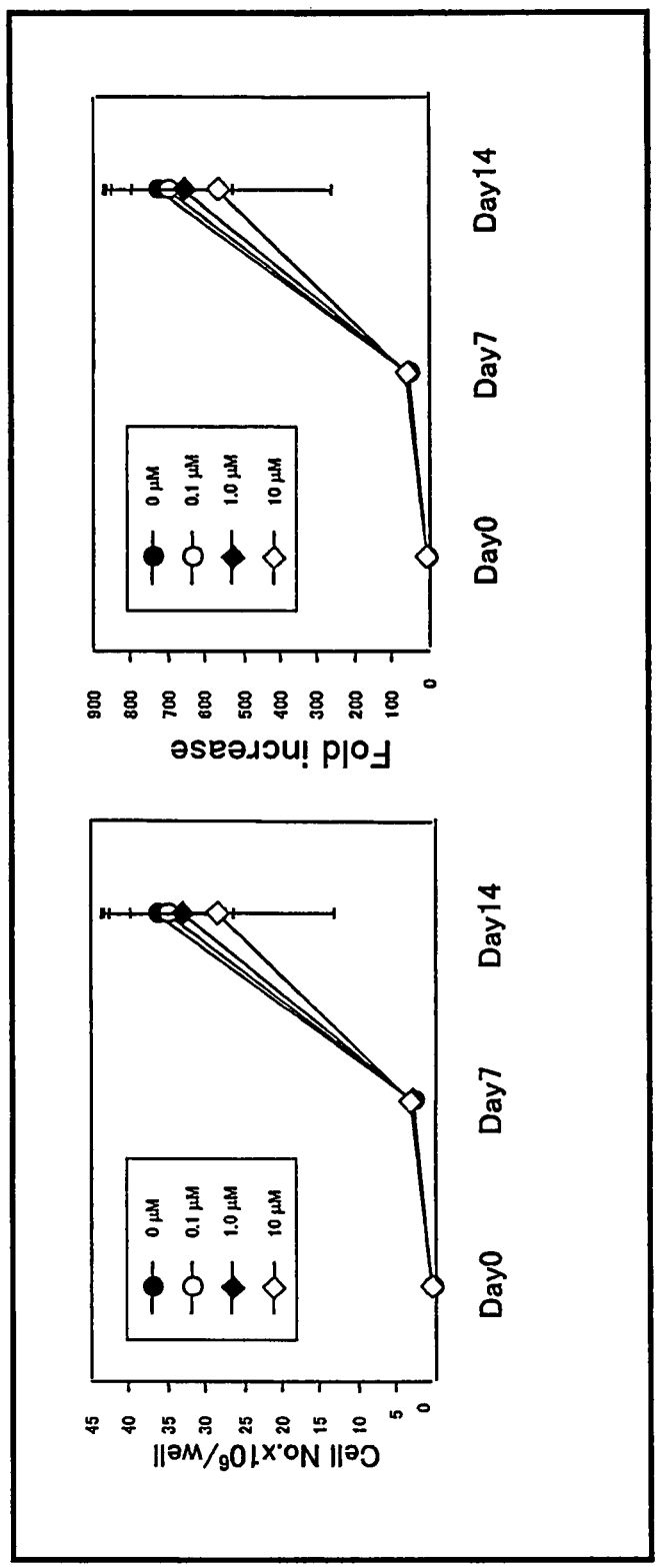
FIG. 2 shows the state of expansion of the cell number when cord blood-derived CD133 positive cells were cultured in the serum-free culture medium of the present invention. The cell numbers at the start of cultivation, after cultivation for 7 days and after cultivation for 14 days are shown. The experiment was performed using four kinds of serum-free culture media containing different concentrations of TGF-β inhibitor.

The obtained CD133 positive cells (also referred to as CD133+cells) were seeded on Primaria Tissue Culture dish (BD Falcon) with 35 mm of diameter at the concentration of $5 \times 10^4$ cells per 1.5 mL of the serum-free culture medium of the present invention produced in the above-mentioned (1), and cultured at 37° C. for 14 days in the presence of 5% $CO_2$. During the culture, the medium was exchanged 7 days later. The state of the cells cultured for 14 days in the serum-free culture medium prepared by the addition of 1 μM TGF-β inhibitor is shown in FIG. 1. In addition, the number of cells after 7 days or 14 days of cultivation in the serum-free culture medium prepared by the addition of 0, 0.1, 1 or 10 μM of TGF-β inhibitor is shown in FIG. 2. The results are shown in the number of cells per well and the expansion ratio relative to the number at the start of cultivation (Day 0).

In the both cases, remarkable expansion of cells was observed.

Example 2

Figure 3:
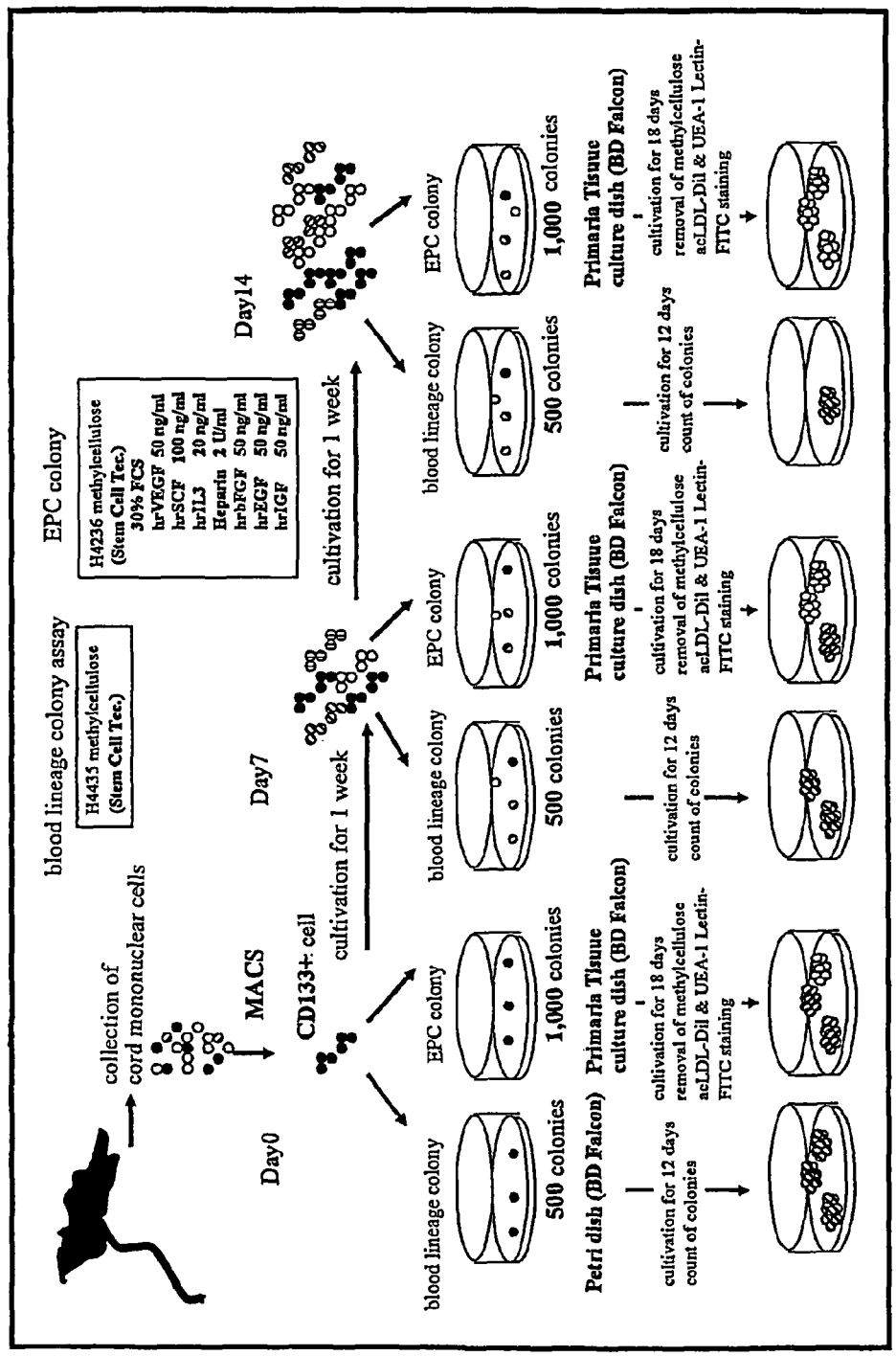
FIG. 3 shows concrete steps for qualitatively evaluation using a methylcellulose medium of a cell expanded by the method of the present invention. Each of the cells at the start of cultivation, after cultivation for 1 week and after cultivation for 2 weeks in the serum-free culture medium of the present invention is subjected to blood lineage colony assay and EPC colony assay.

In Vitro Differentiation and Expansion of Cord Blood CD133 Positive Cell-Derived EPC and Evaluation Thereof Using the serum-free culture media of the present invention containing various concentrations of TGF-β inhibitor as prepared in Example 1, cord blood CD133 positive cell-derived EPC was expanded in vitro and differentiated. The degree of expansion was evaluated by counting the number of colonies, and the degree of differentiation was evaluated by separately counting the number of colonies of blood lineage cell and that of EPC. For EPC colony, moreover, large cell colonies and small cell colonies were separately counted, as well as the total number of EPC colonies was counted. The specific procedures are shown in FIG. 3.

The cord blood-derived mononuclear cells were collected and cultivated in a serum-free culture medium in the same manner as in Example 1. Using the cells at the time points of the start of cultivation, after 1 week of cultivation and after an additional 1 week (total 14 days) of cultivation in the serum-free culture medium, an assay for determination of the colony-forming ability of blood lineage cell (hereinafter to be simply referred to as blood lineage colony assay) and an assay for determination of colony-forming ability of EPC (hereinafter to be simply referred to as EPC colony assay) were performed. For cultivation in the serum-free culture medium, CD133 positive cells isolated by MACS column were first seeded on Primaria Tissue Culture dish (BD Falcon) with 35 mm of diameter at the concentration of $5 \times 10^4$ cells per 1.5 mL of the serum-free culture medium of the present invention, and the cells were cultured at 37° C. for 1 week in the presence of 5% $CO_2$. Furthermore, the obtained expanded cells were collected and reseeded on Primaria Tissue Culture dish (BD Falcon) with 35 mm of diameter at the concentration of $1.25 \times 10^5$ cells per 1.5-2.0 mL of the serum-free culture medium of the present invention and the cells were cultured at 37° C. for 1 week in the presence of 5% $CO_2$.

(Blood Lineage Colony Assay)

Figure 4:
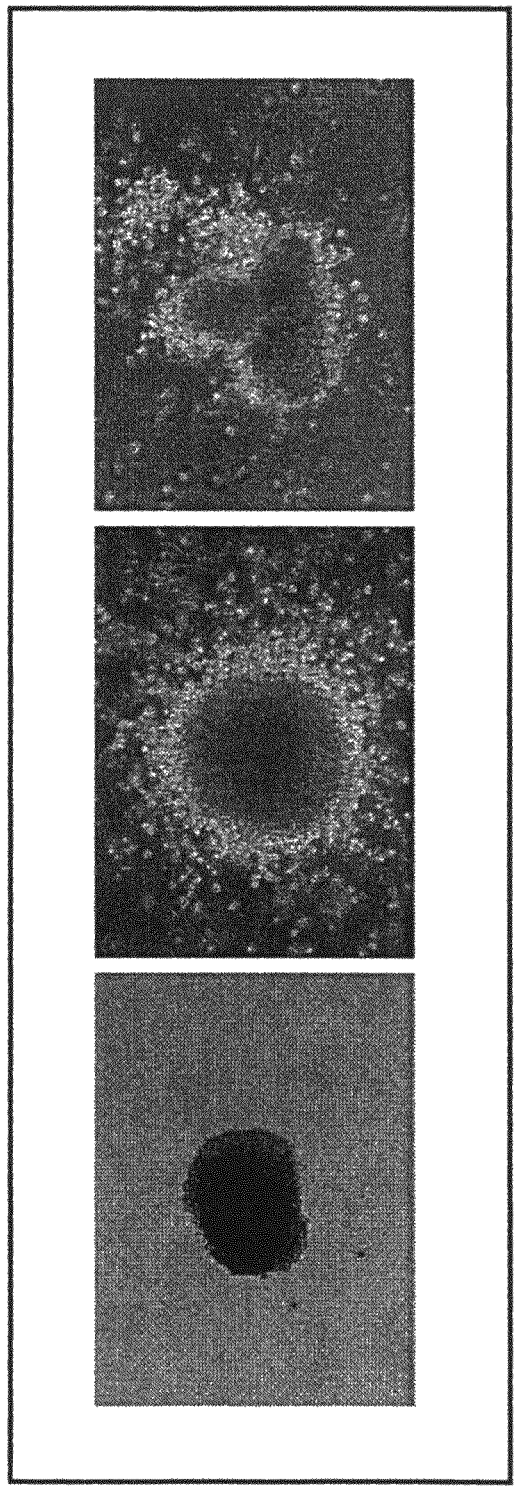
FIG. 4 shows one example of an image of blood cell colony derived from cord blood-derived CD133 positive cell, which is formed by blood cell colony assay using methylcellulose medium.

The cells at each time lapse point were seeded on Petri dish (BD Falcon) with 35 mm of diameter at the concentration of 500 cells per 1 mL and cultured at 37° C. for 12 days in the presence of 5% $CO_2$. After 12 days, the number of colonies observed on the dish was counted. As a result, several kinds of colonies such as erythroid burst-forming unit colony (BFU-E), granulocyte-macrophage lineage colony-forming unit colony (CFU-GM), macrophage colony-forming unit colony (CFU-M), mixed colony (CFU-GEM) and the like were mixed. The colony images of three kinds of colonies, namely, BFU-E colony, CFU-GM colony and CFU-GEM colony, are shown in FIG. 4.

(EPC Colony Assay)

First, a physiologically active substance-containing methylcellulose medium to be used for the assay was prepared. Using a methylcellulose medium (H4236, Stem Cell Tec.), a physiologically active substance-containing methylcellulose medium was prepared according to the composition shown in Table 2. Namely, each ingredient shown in Table 2 was aseptically added to a methylcellulose medium to a given concentration.

TABLE 2

| component | provided by | concentration |
|---|---|---|
| FCS | JRH | 30% |
| hrVEGF | Peprotec | 50 ng/mL |
| hrSCF | Kirin Brewery | 100 ng/mL |
| hrIL-3 | Kirin Brewery | 20 ng/mL |
| heparin | Shimizu Pharmaceutical | 2 U/mL |
| hrbFGF | Peprotec | 50 ng/mL |
| hrEGF | Peprotec | 50 ng/mL |
| hrIGF | Peprotec | 50 ng/mL |

In Table 2, "h" shows human-derived, and "r" shows a recombinant produced gene-engineeringly. Other abbreviations are as mentioned above.

Figure 5:
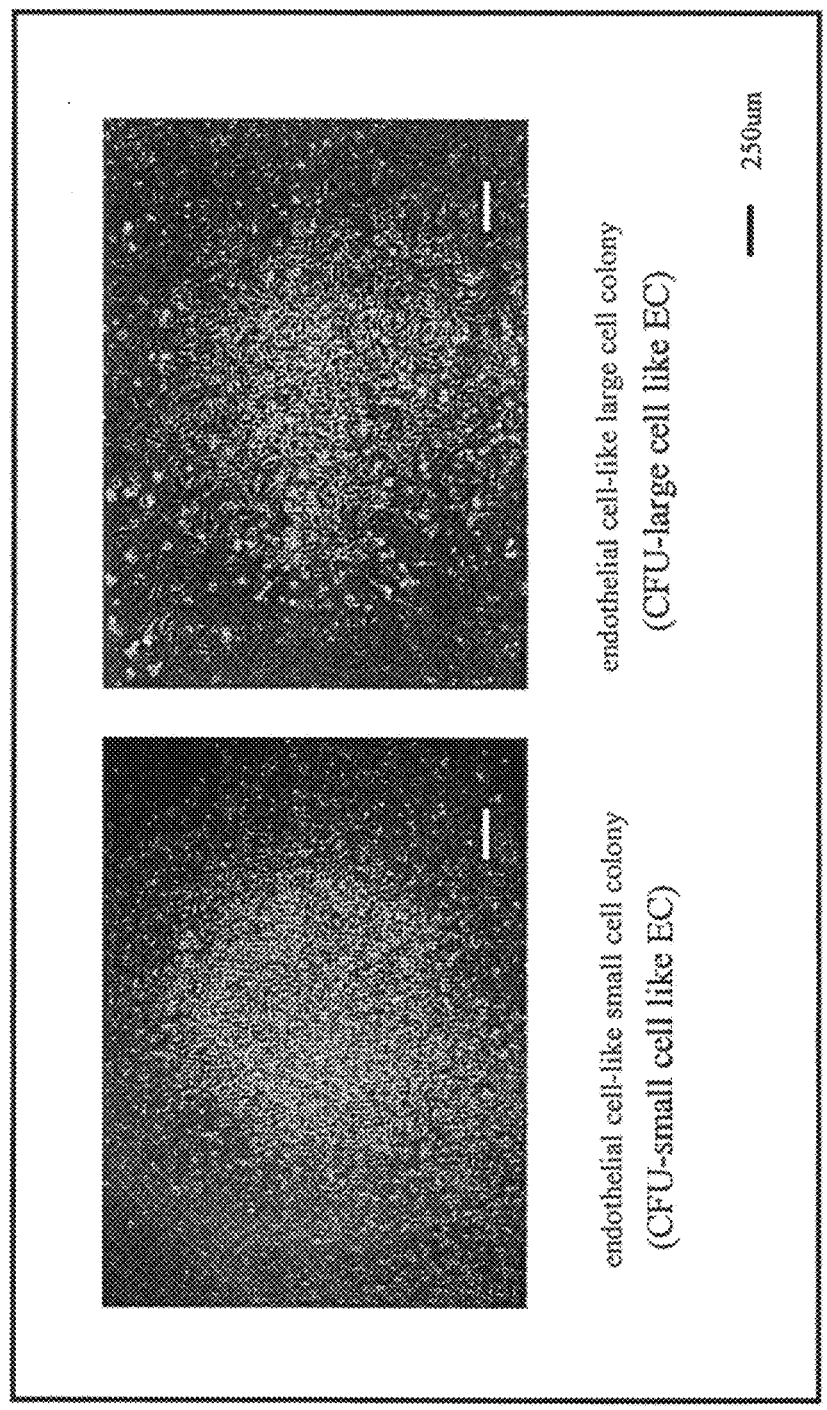
FIG. 5 shows one example of an image of EPC colony derived from cord blood-derived CD133 positive cell, which is formed by EPC colony assay using methylcellulose medium containing a physiologically active substance. Two kinds of EPC colonies having different cell sizes appear after cultivation for 14-18 days.

Next, the cells at each time lapse point, which had been cultured in the serum-free culture medium of the present invention, were cultured in the above-mentioned physiologically active substance-containing methylcellulose medium for 18 days. Then, the methylcellulose medium was removed, and the non-adherent cells were washed away with PBS. The colony of the cells attached to the culture dish was observed to find that two kinds of EPC colonies having different individual cell sizes had appeared. The colony of small cells is conveniently referred to as endothelial cell-like small cell colony (CFU-small cell like EC), and the colony of large cells is conveniently referred to as endothelial cell-like large cell colony (CFU-large cell like EC). FIG. 5 is an image of each colony observed with a phase contrast microscope. These colonies were double-stained with acLDL-DiI and UEA-1 lectin-FITC. For detail, after removal of methylcellulose, 1 ml of EGM-MV-added EBM-2 (5% FCS medium) (Clonetics Co., Single quots kit) was added. Then, acLDL-DiI (10 μl) was added, and the cells were cultured for 3 hr. After washing twice with PBS, the above-mentioned medium and FITC labeled-UEA1 lectin (manufactured by Sigma) were added to the medium to a concentration of 0.2 μg/ml, and the medium was cultured for 3 hr. After washing twice, the medium was exchanged and the cells were observed with a fluorescence microscope.

Figure 6:
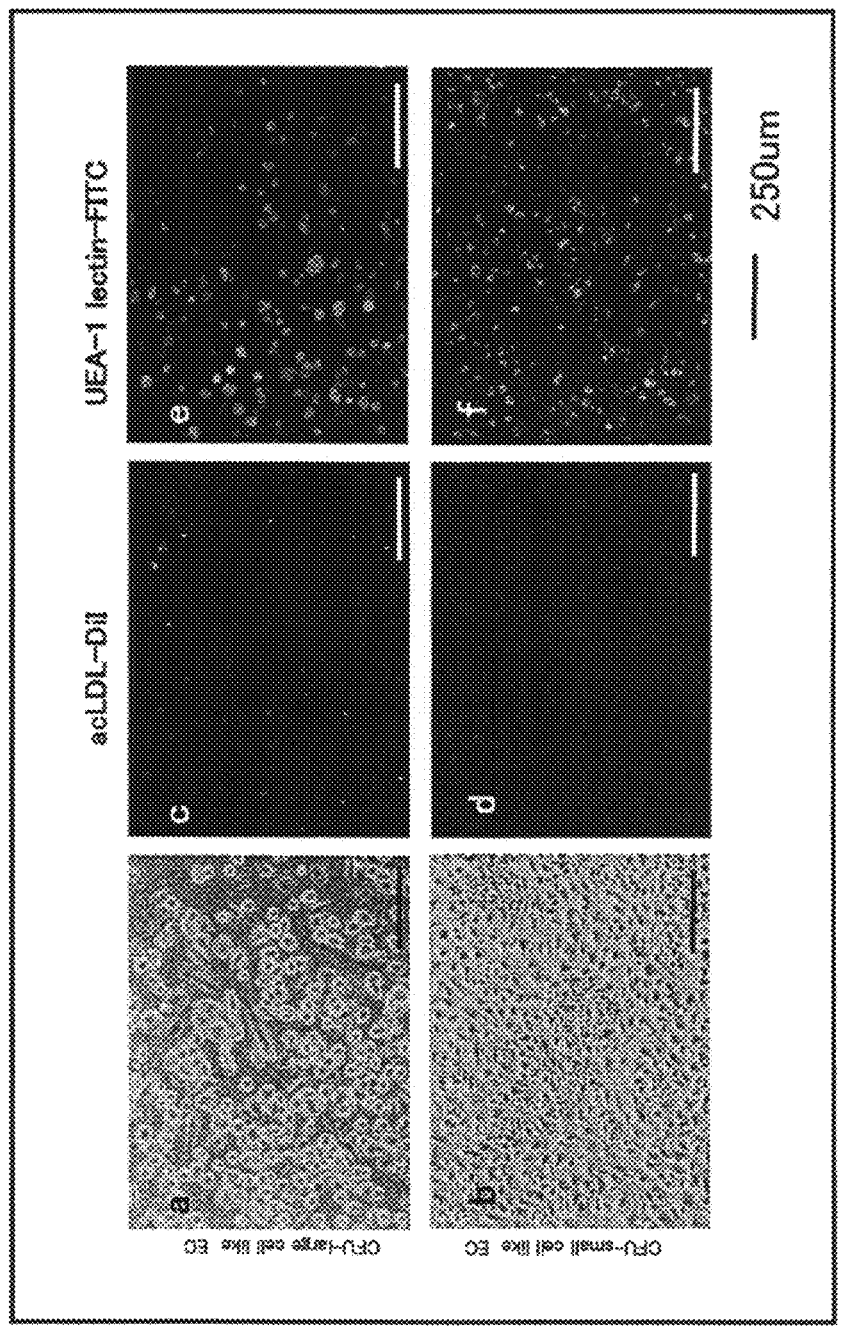
FIG. 6 shows the results of double staining of EPC colony derived from cord blood CD133 positive cell with acLDL-DiI and UEA-1 lectin-FITC, wherein a, c and e each show a large cell colony, b, d and f each show a small cell colony, a and b each show a phase-contrast image, c and d each show an image stained with acLDL-DiI, and e and f each show an image stained with UEA-1 lectin-FITC. Both colonies were stained with acLDL-DiI and UEA-1 lectin-FITC, and exhibited a feature of EPC.

The results are shown in FIG. 6. Both colonies were stained with acLDL-DiI and UEA-1 lectin-FITC, and exhibited the characteristics of EPC.

The number of colonies confirmed to be the EPC colonies was counted. The total number of colonies, the number of small cell colonies and the number of large cell colonies were separately counted.

(Results)

Figure 7:
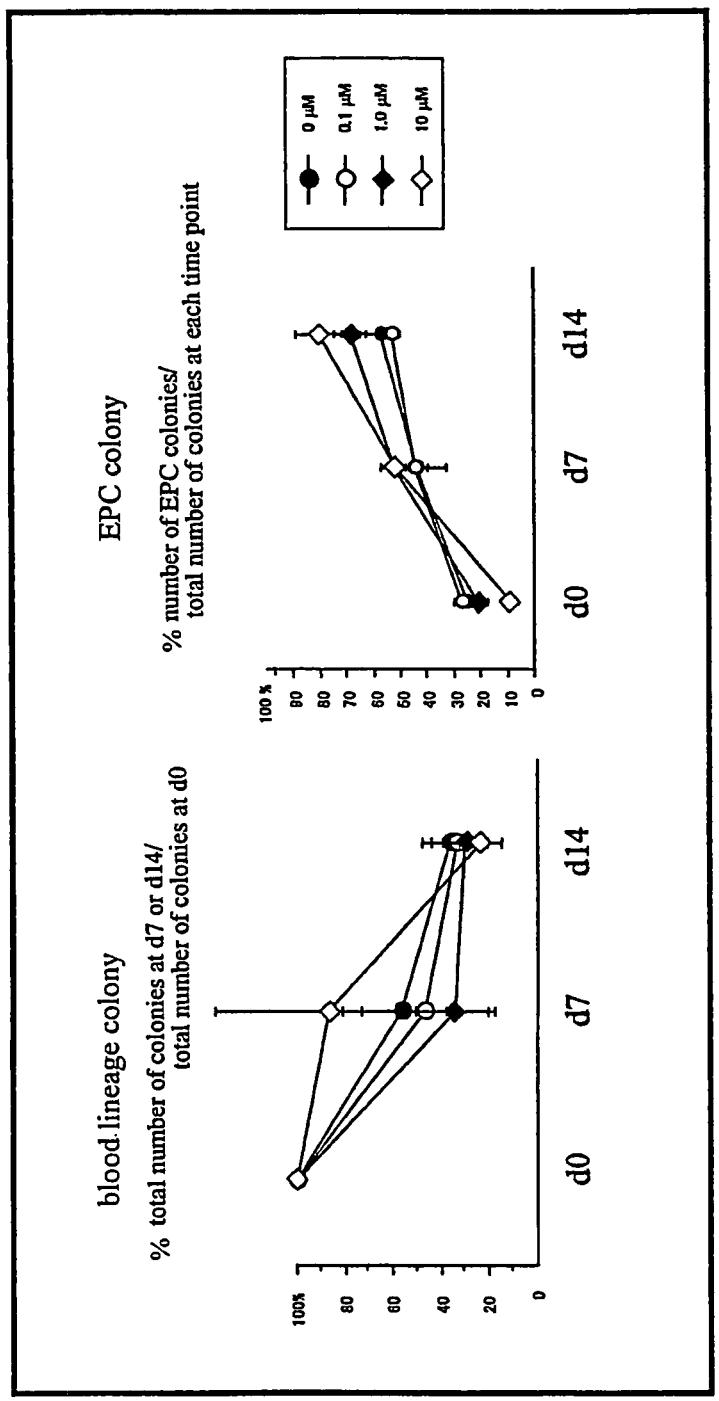
FIG. 7 shows the results of time-course measurement of the frequency of blood lineage colony and EPC colony formation, that accompanied expansion and cultivation in the serum-free culture medium of the present invention. The experiment was performed using four kinds of serum-free culture media containing different concentrations of TGF-β inhibitor. In the cultivation by the method of the present invention, the frequency of blood colony formation decreased and the frequency of EPC colony formation increased.

For the blood lineage colony, the number of colonies of four kinds of colonies: erythroid burst-forming unit colony (BFU-E), granulocyte-macrophage lineage colony-forming unit colony (CFU-GM), macrophage colony-forming unit colony (CFU-M) and mixed colony (CFU-GEM) was added, and the appearance frequency thereof was determined over time. For EPC colony, the number of colonies of small cell colonies and large cell colonies were added, and the appearance frequency thereof was determined over time. As the total number of colonies, moreover, the number of colonies of CFU-GM, CFU-M, small cell colonies and large cell colonies were added. For blood lineage colony, the proportion of the number of colonies formed from cells at 7 or 14 days after the start of cultivation relative to the number of colonies formed from cord blood-derived CD133 positive mononuclear cells at the start of cultivation in the serum-free culture medium is shown in %. For EPC colony, the proportion of the number of EPC colonies relative to the total number of colonies at the start of cultivation, at 7 days and 14 days after the start of cultivation in the serum-free culture medium is shown in %. The results are shown in FIG. 7.

According to the cultivation method using the method of the present invention, the EPC colony appearance frequency increases as the blood lineage colony appearance frequency decreases.

Figure 8:
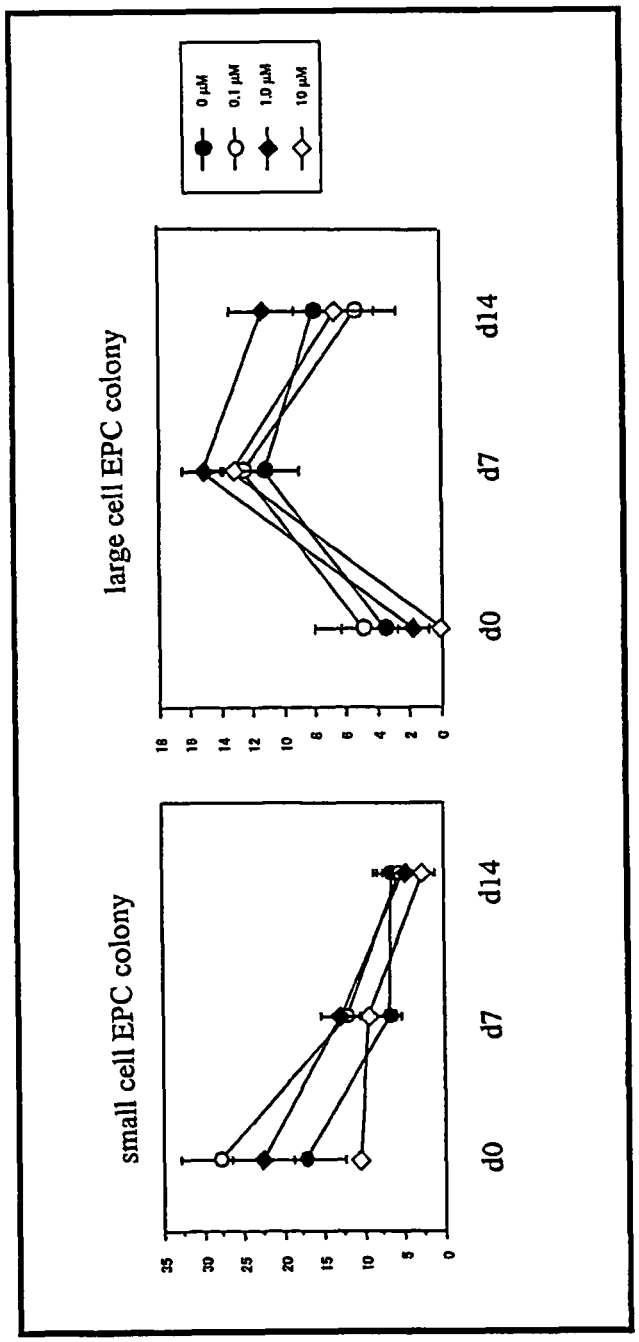
FIG. 8 shows the results of measurement of the shift of small cell EPC colony-forming ability and large cell EPC colony-forming ability, that accompanied expansion and cultivation in the serum-free culture medium of the present invention. The experiment was performed using four kinds of serum-free culture media containing different concentrations of TGF-β inhibitor. Small cell EPC colonies showed a tendency toward gradual decrease by various concentrations of TGF-β inhibitor. In contrast, large cell EPC colonies reached maximum 1 week later and showed a tendency toward slight decrease 2 weeks later.

For EPC colony, moreover, the number of small cell EPC colonies and the number of large cell EPC colonies were determined. The results are shown in FIG. 8. While the small cell EPC colonies showed a tendency toward a gradual decrease with cultivation in the serum-free culture medium, the large cell EPC colonies showed a peak after cultivation for 1 week and a tendency toward a slight decrease after 2 weeks of cultivation.

Figure 9:
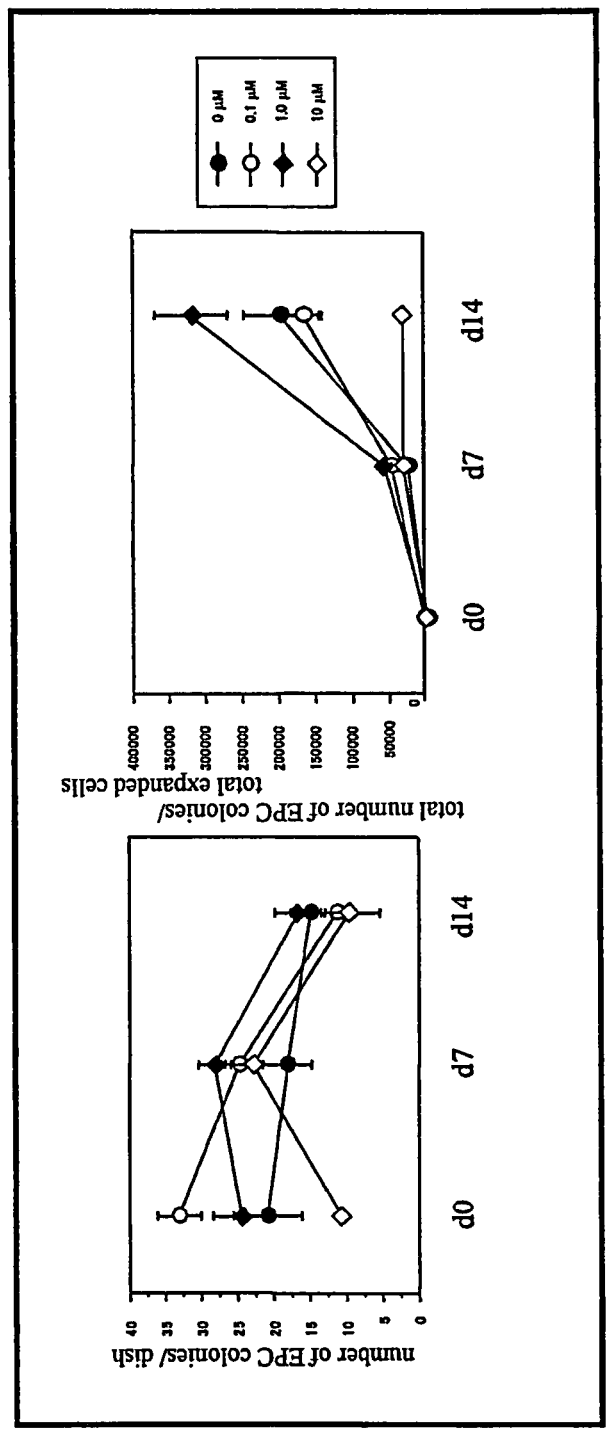
FIG. 9 shows the results of measurement of the shift of EPC colony-forming ability, that accompanied expansion and cultivation in the serum-free culture medium of the present invention. When cultivation was performed using the serum-free culture media containing various concentrations of TGF-β inhibitor, the number of EPC colonies per Dish and the total number of EPC colonies after cultivation for 2 weeks were at maximum in the medium containing 1 μM of TGF-β inhibitor.

In addition, an influence of the concentration of TGF-β inhibitor added to each serum-free culture medium on the number of EPC colonies was examined. The results are shown in FIG. 9. It is shown in the number of EPC colonies per culture dish used for the assay and the total number of EPC colonies formed from the whole expanded cells. After cultivation in the serum-free culture medium of the present invention for 2 weeks, cultivation in the serum-free culture medium containing 1 μM of TGF-β inhibitor resulted in the formation of the largest number of EPC colonies both in terms of the number of EPC colonies per Dish and the total number of EPC colonies.

Example 3

Examination of Effectiveness for Cell Transplantation Therapy

CD133 positive cell free of expansion and differentiation induction, and EPC cell expansion and differentiation induced by the method of the present invention were each used for cell transplantation therapy of ischemic cardiac diseases, and the effectiveness thereof was examined. The effectiveness was examined by determining the contractile function and diastolic function.

(1) Cell Transplantation Using CD133 Positive Cell Free of Expansion and Differentiation Induction By the same procedures as in Example 1 (2), CD133 positive cells were collected. Then, an ischemic myocardium model rat was prepared. In detail, under Nembutal anesthesia, a nude rat was subjected to the 3rd or 4th left posterior intercostal thoracotomy, and the epicardium was detached. Subsequently, the region just below left atrial appendage of left anterior descending coronary artery of the exposed heart was ligated, and the resulting nude rat was used as an ischemic myocardium model. The CD133 positive cells obtained as mentioned above were transplanted to three sites in the infarct marginal region of the nude rat at the dose of $1 \times 10^5$ cells/100 μL PBS/rat or $5 \times 10^5$ cells/100 μL PBS/rat. At 4 weeks after the transplantation, the cardiac function was evaluated.

(2) Cell Transplantation Using EPC Cell Subjected to Expansion and Differentiation Induction CD133 positive cells isolated in the same manner as in the above-mentioned (1) were seeded on a 35 mm diameter Primaria Tissue Culture dish (BD Falcon) at a concentration of $5 \times 10^4$ cells per 1.5 mL of the serum-free culture medium of the present invention, and the cells were cultured at 37° C. for 1 week in the presence of 5% $CO_2$. Furthermore, the obtained expanded cells were reseeded on a 35 mm diameter Primaria Tissue Culture dish (BD Falcon) at a concentration of $1.25 \times 10^5$ cells per 1.5-2.0 mL of the serum-free culture medium of the present invention, and the cells were cultured at 37° C. for 1 week in the presence of 5% $CO_2$.

For the serum-free culture medium, the serum-free culture medium of the present invention containing various concentrations of TGF-β inhibitor prepared in Example 1 was used.

The obtained EPC cells after in vitro expansion and differentiation were transplanted to 3 sites in the infarct marginal region of a nude rat (similar to the one mentioned above) at a dose of $1 \times 10^5$ cells/100 μL PBS/rat or $5 \times 10^5$ cells/100 μL PBS/rat. At 4 weeks after the transplantation, the cardiac function was evaluated.

(3) Results

Figure 10:
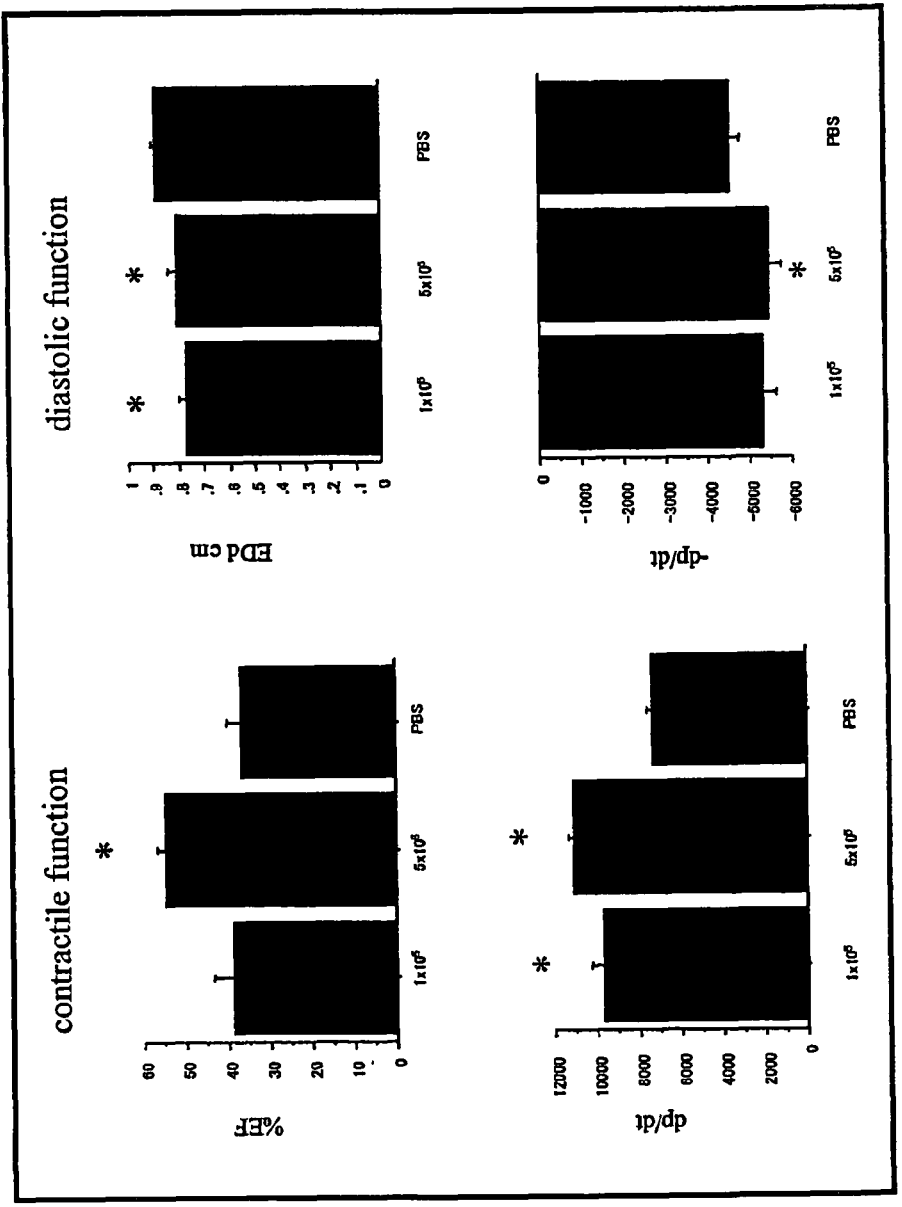
FIG. 10 shows the results of the evaluation of the effectiveness of cell transplantation therapy on ischemic cardiac diseases, when a non-expanded CD133 positive cell was transplanted, wherein * shows a significant difference ($P<0.05\%$) relative to the control (PBS single administration group).
Figure 11:
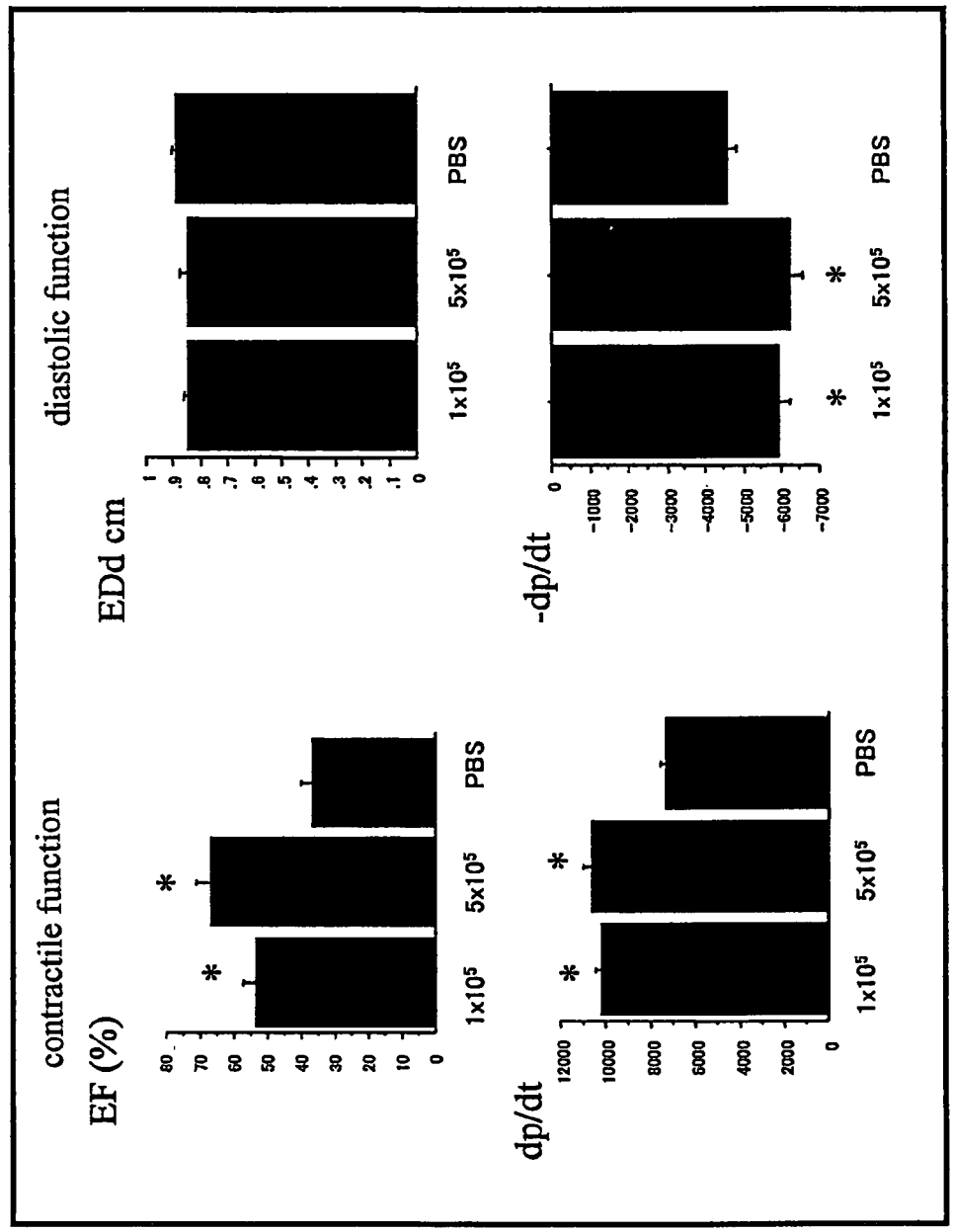
FIG. 11 shows the results of the evaluation of the effectiveness of cell transplantation therapy on ischemic cardiac diseases, when an EPC expanded in vitro by cultivation in the serum-free culture medium of the present invention was transplanted, wherein * shows a significant difference ($P<0.05\%$) relative to the control (PBS single administration group).

The results of transplantation of CD133 positive cell free of expansion and differentiation induction are shown in FIG. 10, and the results of transplantation of EPC cell after expansion and differentiation induction are shown in FIG. 11.

The cell transplantation using the cells expanded by the method of the present invention improved the cardiac function, particularly the contractile function in ischemic cardiac diseases.

INDUSTRIAL APPLICABILITY

By transplantation of the cells expanded by the method of the present invention, the cardiac function (contractile function and diastolic function) in ischemic cardiac diseases was improved. That is, the method of the present invention is considered to be useful for both qualitative and quantitative production of an endothelial lineage cell, and can be a useful method for a cell transplantation therapy targeting a vascular disorder such as ischemic cardiac disease and the like.

This application is based on a patent application No. 2005-047816 filed in Japan (filing date: Feb. 23, 2005), the contents of which are incorporated in full herein by this reference.

The invention claimed is:

1. A method for preparing endothelial progenitor cells, which comprises incubating CD34 positive and/or CD133 positive cells in a serum-free culture medium containing stem cell factor, interleukin-6, FMS-like tyrosine kinase 3 ligand, thrombopoietin and vascular endothelial growth factor, whereby the number of endothelial progenitor cells contained in the CD34 positive and/or CD133 positive cells is increased.

2. The method of claim 1, wherein the CD34 positive and/or CD133 positive cells include mononuclear cells including endothelial progenitor cells.

3. The method of claim 2, wherein the CD34 positive and/or CD133 positive cells are prepared from bone marrow fluid, cord blood or peripheral blood.

4. The method of claim 1, wherein the CD34 positive and/or CD133 positive cells include endothelial progenitor cells.

5. The method of claim 4, wherein the CD34 positive and/or CD133 positive cells are prepared from bone marrow fluid, cord blood or peripheral blood.

6. The method of claim 1, wherein the CD34 positive and/or CD133 positive cells, stem cell factor, interleukin-6, FMS-like tyrosine kinase 3 ligand, thrombopoietin, and vascular endothelial growth factor are all obtained from animals of a single species.

7. The method of claim 1, wherein the CD34 positive and/or CD133 positive cells are derived from human.

8. The method of claim 1, wherein the serum-free culture medium further comprises transforming growth factor β inhibitor.

* * * * *